US00PP29619P3

(12) United States Plant Patent
Suphachadiwong

(10) Patent No.: US PP29,619 P3
(45) Date of Patent: Aug. 21, 2018

(54) ***SANSEVIERIA* PLANT NAMED 'SUPSAN1603'**

(50) Latin Name: *Sansevieria cylindrica*
Varietal Denomination: SUPSAN1603

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,329

(22) Filed: Oct. 25, 2017

(65) Prior Publication Data

US 2018/0124986 P1 May 3, 2018

(30) Foreign Application Priority Data

Oct. 31, 2016 (QZ) ..... PBR 2016/2650

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
CPC ..... A01H 5/12; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Sansevieria* plant named 'SUPSAN1603' which is characterized by the combination of a compact equitant growth habit, a broad obovate plant form with a very slightly spiraling aspect, broad succulent foliage which is terete and axially grooved, decurrent leaf bases with prominent light yellow-green margins, dark green foliage with light greyed-green radial bands, and the stability of all characteristics from generation to generation.

2 Drawing Sheets

Latin name of the genus and species: The Latin name of the genus and species of the novel variety disclosed herein is *Sansevieria cylindrica.*

Variety denomination: The inventive variety of *Sansevieria* disclosed herein has been given the variety denomination 'SUPSAN1603'.

CROSS REFERENCE TO RELATED APPLICATIONS

This application claims priority to the Community Plant Variety Rights application number 2016/2650, filed Oct. 31, 2016, which is herein incorporated by reference.

BACKGROUND OF THE INVENTION

Parentage: The *Sansevieria* variety 'SUPSAN1603' originated as a seedling selection from the controlled pollination of the proprietary seed parent, *Sansevieria cylindrica* 'MXU1807' (not patented), with the proprietary pollen parent, *Sansevieria cylindrica* 'MXU1804' (not patented). Both parents were developed by, and are owned by, the inventor and were never commercially released. Said crossing was conducted by the inventor in a small, netted greenhouse in Chonburi, Thailand in November of 2006. Seeds from said cross were harvested, then germinated, and the resulting seedlings were grown to a mature size in order to evaluate for a desirable combination of commercial characteristics. In November of 2008, one candidate plant was observed to exhibit a unique growth habit and leaf coloration. After confirmation of the distinctness and stability of the characteristics first observed, the inventor selected the new *Sansevieria* cultivar, 'SUPSAN1603', for commercial introduction.

Asexual Reproduction: Asexual reproduction of 'SUPSAN1603' by way of harvesting vegetative ground shoots was first initiated in November of 2008 at Chonburi, Thailand. Access to all plants was restricted, as plants were kept in a greenhouse not open to the public. Through subsequent propagation of vegetative ground shoots, five generations have been reproduced which have shown that the unique features of this cultivar are stable and reproduced true to type.

SUMMARY OF THE INVENTION

The cultivar 'SUPSAN1603' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'SUPSAN1603'. These characteristics in combination distinguish 'SUPSAN1603' as a new and distinct *Sansevieria* cultivar:

1. *Sansevieria* 'SUPSAN1603' exhibits a compact equitant growth habit; and
2. *Sansevieria* 'SUPSAN1603' exhibits a vertically flattened, broad obovate plant form with a very slightly spiraling aspect; and
3. *Sansevieria* 'SUPSAN1603' exhibits broad succulent foliage which is terete and axially grooved; and
4. *Sansevieria* 'SUPSAN1603' exhibits decurrent leaf bases with prominent light yellow-green margins; and 5. *Sansevieria* 'SUPSAN1603' exhibits dark green foliage with light greyed-green radial bands.

BOTANICAL DESCRIPTION OF THE PLANT

Figure 1:
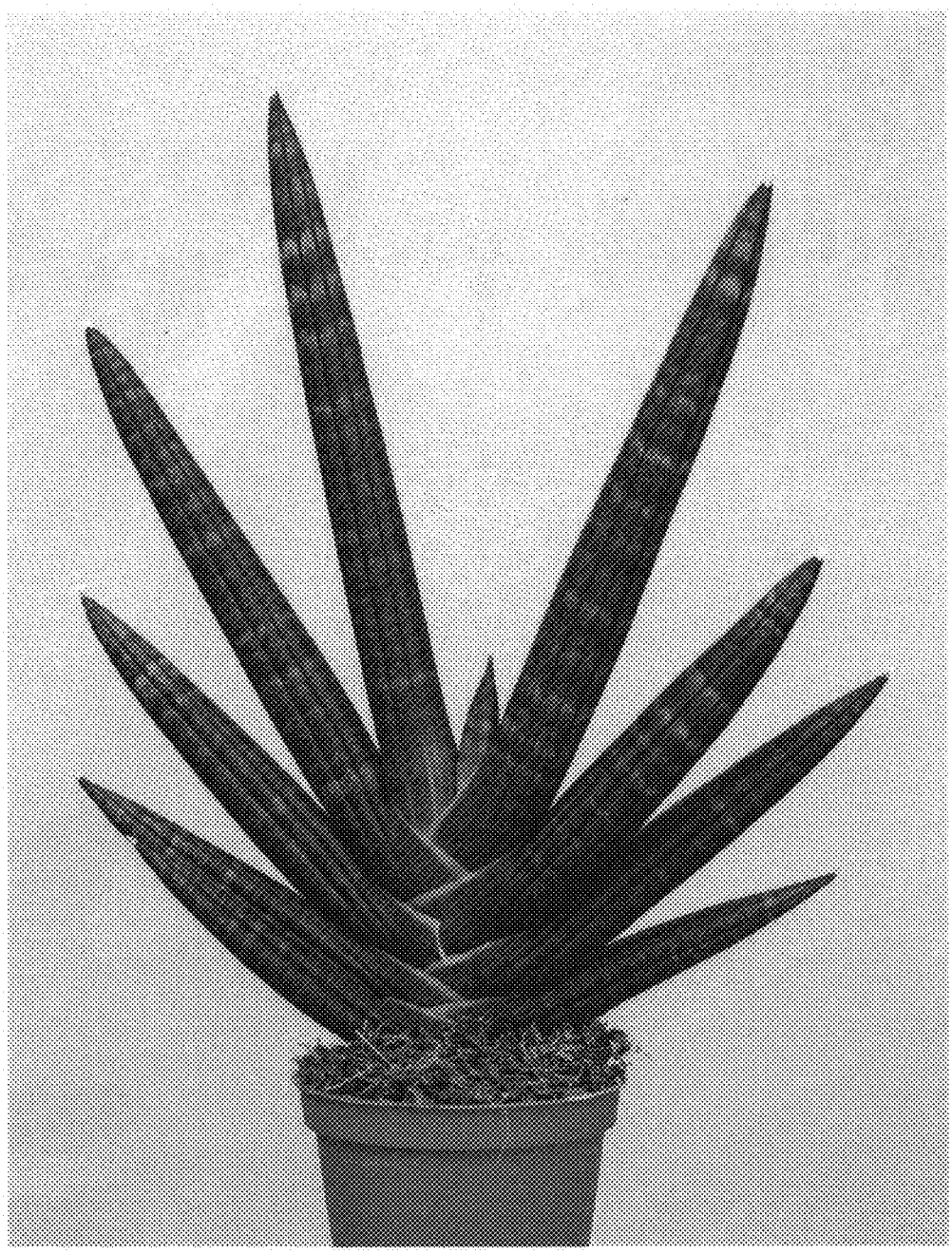
FIG. 1 illustrates, as nearly true as it is reasonably possible to make the same in color photographs of this type, an exemplary plant of 'SUPSAN1603' grown in a commercial greenhouse in Chonburi, Thailand. This plant is approximately 12 months old, shown planted in an 8 cm container.
Figure 2:
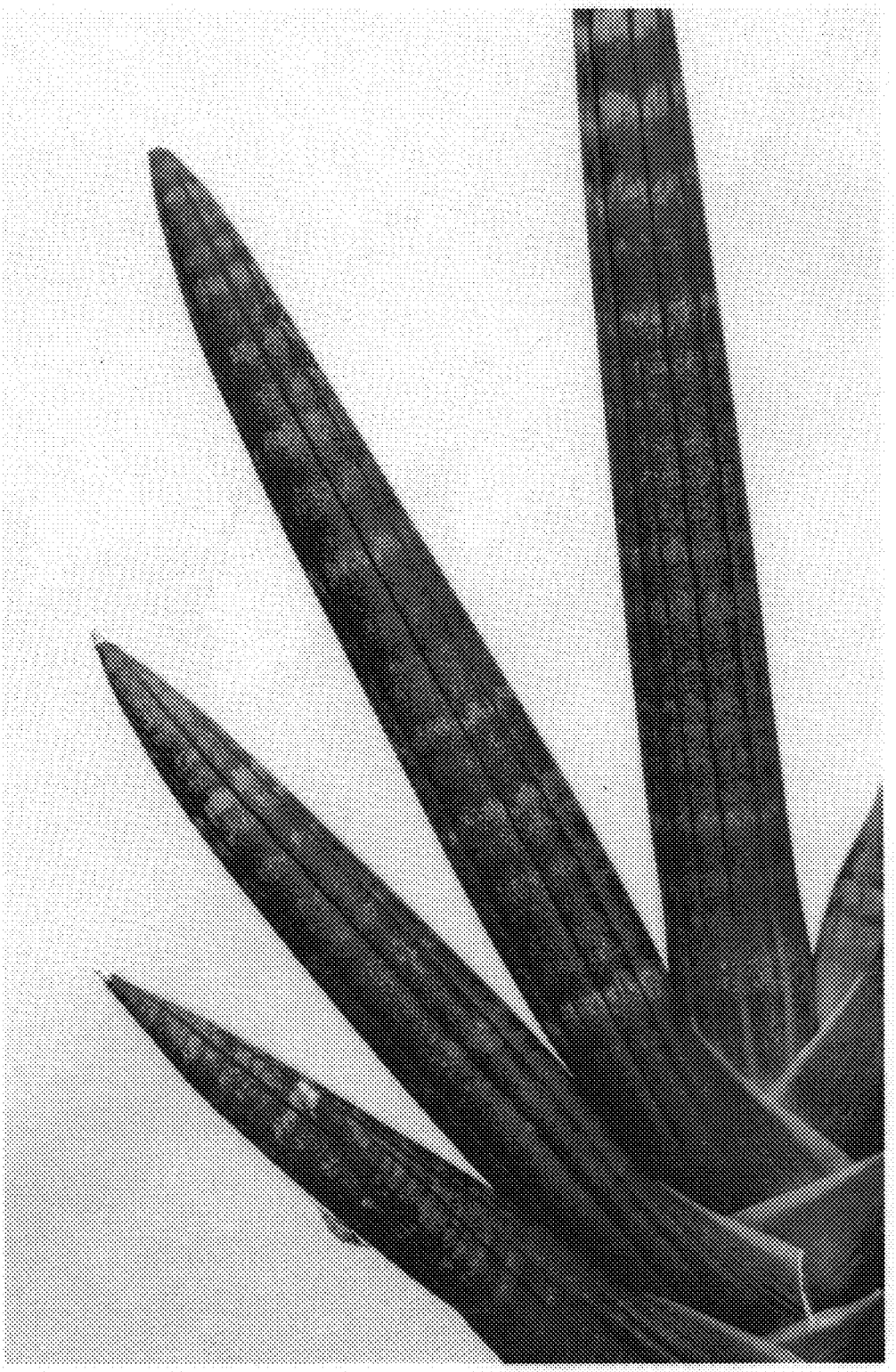
FIG. 2 illustrates, as nearly true as it is reasonably possible to make the same in color photographs of this type, the typical foliage of 'SUPSAN1603'.

The following observations and measurements, made in October of 2017, describe averages from a sample set of six specimens of 12 month old 'SUPSAN1603' plants grown in 8 cm containers, at a commercial greenhouse in Chonburi, Thailand. The plants were grown using conventional greenhouse production protocols for *Sansevieria* plants which consisted of overhead irrigation, 50% shade cloth, and no fertilizer. No photoperiodic or chemical treatments were given to the plants.

Those skilled in the art will appreciate that certain characteristics will vary with older or, conversely, with younger plants. 'SUPSAN1603' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SUPSAN1603' and comparisons with the parents and most similar commercial variety of *Sansevieria* are provided below.

Plant description:

*Growth habit*.—Monopodial perennial; equitant, compact, and upright to outward.

*Plant form*.—Vertically flattened with a very slightly spiraling aspect; broad obovate at the widest point.

*Average height*.—23.7 cm.

*Plant spread*.—7.6 cm at the narrowest point, and 20.2 cm at the widest point.

*Plant vigor*.—Low to moderate.

*Growth rate*.—Moderate.

*Propagation type*.—Division of vegetative ground shoots; harvesting ground shoots from the mother plant.

*Propagation details*.—The time needed to root a shoot division is approximately 2 to 3 months with temperatures ranging from approximately 17 to 40 degrees Celsius.

*Disease/pest resistance*.—Plants have not been observed to be susceptible or resistant to pathogens and pests common to *Sansevieria*.

*Environmental tolerances*.—Adapt to, at least, USDA Zones 10 and 12 and temperatures as high as 40 degrees Celsius; moderate tolerance to rain; moderate to high tolerance to wind.

Root system:

*General*.—Moderately dense and moderately branched rooting; roots are slightly fibrous.

*Distribution in the soil profile*.—Shallow to moderately deep.

*Diameter of roots*.—0.15 cm on average.

*Texture*.—Smooth; no root hairs.

*Color*.—Greyed-yellow, nearest to RHS 162C.

Stem:

*Branching habit*.—Monopodial, equitant; decurrent leaf bases form the stem.

*Number of primary (main) stems per plant*.—One.

*Number of secondary (lateral) branches per plant*.—None.

*Appearance and shape*.—Stem is not visible; decurrent leaf bases form the stem.

*Length*.—The decurrent leaf bases collectively have an average length of 5.5 cm.

*Diameter*.—The decurrent leaf bases collectively have an average diameter of 1.9 cm.

*Internode length*.—0.6 cm.

Foliage:

*Arrangement*.—Distichous.

*Attachment*.—Decurrent.

*Division*.—Simple.

*Quantity*.—9.

*Attitude*.—Upright to outward; at an average angle of 45 degrees to vertical.

*Lamina*.—Dimensions — 16.5 cm long and 1.5 cm wide. Thickness — Approximately 1.9 cm. Shape of blade — Linear; succulent. Cross-section — Terete and axially grooved with an average of 9 undeep grooves. Aspect — Nearly straight. Apex — Acute with a papery tip which is colored greyed-white, nearest to in between RHS 156C and 156D. Base — Decurrent. Margin — Leaves are terete so there are no margins, with the exception of the leaf base; leaf base margins are entire. Texture of upper surface — Glabrous; axially grooved. Texture of lower surface — Glabrous; axially grooved. Luster of the upper surface — Matte. Luster of the lower surface — Matte. Color — Juvenile foliage, upper surface — Green, nearest to RHS NN137A, with mottled radial bands colored greyed-green, nearest to RHS 195B. Juvenile foliage, lower surface — Green, nearest to RHS NN137A, with mottled radial bands colored greyed-green, nearest to RHS 195B; the base is yellow-green, nearest to RHS 144D. Mature foliage, upper surface — Nearest to in between green, RHS NN137A, and greyed-green, RHS N189A, with mottled radial bands colored yellow-green, nearest to RHS 147C. Mature foliage, lower surface — Nearest to in between green, RHS NN137A, and greyed-green, RHS N189A, with mottled radial bands colored yellow-green, nearest to RHS 147C; the base is nearest to in between yellow-green, RHS 147A, and greyed-green, RHS N189A, but slightly darker; margins of the decurrent base are yellow-green, nearest to RHS 145B. Venation — Pattern — Parallel. Color, upper surface — Greyed-green, nearest to RHS N189A. Color, lower surface — Greyed-green, nearest to RHS N189A.

*Petiole*.—No petioles present, leaves are decurrent.

Inflorescence: No flowering has been observed to date.

Comparisons With the Parent Plants

Plants of the new cultivar 'SUPSAN1603' differ from the seed parent, *Sansevieria* 'MXU1807' (not patented), by the characteristics described in Table 1.

Comparison Between 'Supsan1603' and 'MXU1807'

TABLE 1

| Characteristic | 'SUPSAN1603' | 'MXU1807' |
|---|---|---|
| Overall plant size. | Smaller than 'MXU1807'. | Larger than 'SUPSAN1603'. |
| Rate of growth. | Faster growing than 'MXU1807'. | Slower growing than 'SUPSAN1603'. |
| Leaf thickness. | Thinner than 'MXU1807'. | Thicker than 'SUPSAN1603'. |
| Leaf length. | Shorter than 'MXU1807'. | Longer than 'SUPSAN1603'. |
| General coloration of the foliage. | Darker green. | Lighter green. |
| Leaf pattern. | More prominent greyed-green radial banding. | Less prominent greyed-green radial banding. |

Plants of the new cultivar 'SUPSAN1603' differ from the pollen parent, *Sansevieria* 'MXU1804' (not patented), by the characteristics described in Table 2.

Comparison Between 'Supsan1603' and 'MXU1804'

TABLE 2

| Characteristic | 'SUPSAN1603' | 'MXU1804' |
|---|---|---|
| Growth habit. | More compact than 'MXU1804'. | Less compact than 'SUPSAN1603'. |
| Rate of growth. | Slower growing than 'MXU1804'. | Faster growing than 'SUPSAN1603'. |
| Leaf thickness. | Thinner than 'MXU1804'. | Thicker than 'SUPSAN1603'. |

TABLE 2-continued

| Characteristic | 'SUPSAN1603' | 'MXU1804' |
|---|---|---|
| Leaf length. | Shorter than 'MXU1804'. | Longer than 'SUPSAN1603'. |
| General coloration of the foliage. | Darker green. | Lighter green. |

Comparison With the Most Similar *Sansevieria* Cultivar Known to the Inventor Plants of the new cultivar 'SUPSAN1603' are most similar to the commercial cultivar, *Sansevieria cylindrica* 'SAN201202' (U.S. Plant Pat. No. 24,457). A comparison of 'SUPSAN1603' with 'SAN201202' is described in Table 3.

Comparison Between 'Supsan1603' and 'San201202'

TABLE 3

| Characteristic | 'SUPSAN1603' | 'SAN201202' |
|---|---|---|
| Growth habit. | More compact than 'SAN201202'. | Less compact than 'SUPSAN1603'. |
| Leaf attitude. | More upright. | Less upright. |
| Leaf thickness. | Thinner than 'SAN201202'. | Thicker than 'SUPSAN1603'. |
| Leaf length. | Shorter than 'SAN201202'. | Longer than 'SUPSAN1603'. |
| Leaf apex. | More pointed. | Less pointed. |
| General coloration of the foliage. | Generally exhibits an overall dark green appearance. | Generally exhibits an overall light greyed-green appearance. |
| Leaf pattern. | Radial bands are narrower than those of 'SAN201202'. | Radial bands are wider than those of 'SUPSAN1603'. |

That which is claimed is:

1. A new and distinct variety of *Sansevieria* plant named 'SUPSAN1603', substantially as described and illustrated herein.

* * * * *